(12) United States Patent
Daniel

(10) Patent No.: US 8,148,156 B1
(45) Date of Patent: Apr. 3, 2012

(54) SYNTHETIC URINE AND METHOD FOR MANUFACTURING SYNTHETIC URINE

(76) Inventor: Brady Alfred Daniel, Visalia, CA (US)

( * ) Notice: Subject to any disclaimer, the term of this patent is extended or adjusted under 35 U.S.C. 154(b) by 0 days.

(21) Appl. No.: 12/590,708

(22) Filed: Nov. 12, 2009

(51) Int. Cl.
*G01N 31/00* (2006.01)
*G01N 33/48* (2006.01)

(52) U.S. Cl. .............. 436/8; 436/18; 436/166; 436/174; 436/176; 252/408.1

(58) Field of Classification Search .............. 436/8, 18, 436/174, 176, 164, 166; 252/408.1
See application file for complete search history.

(56) References Cited

U.S. PATENT DOCUMENTS

| | | |
|---|---|---|
| 3,880,646 A | 4/1975 | Mc Connell et al. |
| 4,146,644 A | 3/1979 | Griffith et al. |
| 4,714,564 A | 12/1987 | Lynch et al. |
| 4,825,851 A | 5/1989 | Cocks et al. |
| 4,989,607 A | 2/1991 | Keusch et al. |
| 5,036,013 A | 7/1991 | Wood et al. |
| 5,105,007 A | 4/1992 | Adamczyk et al. |
| 5,176,668 A | 1/1993 | Bernardin |
| 5,328,954 A | 7/1994 | Sarangapani |
| 5,489,281 A | 2/1996 | Watanabe et al. |
| 5,651,778 A | 7/1997 | Melius et al. |
| 5,993,840 A | 11/1999 | Fawkes et al. |
| 6,046,377 A * | 4/2000 | Huntoon et al. .............. 604/368 |
| 6,306,422 B1 | 10/2001 | Batich et al. |
| 6,716,632 B1 | 4/2004 | Dorn |
| 7,109,035 B2 * | 9/2006 | Haddad .............................. 436/8 |
| 7,192,776 B2 | 3/2007 | Stephens |
| 2002/0106807 A1 | 8/2002 | Novinski et al. |
| 2004/0077106 A1 | 4/2004 | Haddad |

\* cited by examiner

*Primary Examiner* — Maureen Wallenhorst
(74) *Attorney, Agent, or Firm* — Marcus Risso; Risso & Associates

(57) ABSTRACT

A synthetic urine solution is described. The synthetic urine solution is a shelf stable, food grade composition formed of water having a pH between 3 and 10. A thickening agent is dissolved within the water to form a solution having a specific gravity between 1.025 g/cm$^3$ and 1.225 g/cm$^3$. To provide a realistic appearance and odor, a coloring agent and urea are dissolved within the solution. Finally, to provide a shelf stable product, a preservative is also dissolved within the solution.

16 Claims, 1 Drawing Sheet

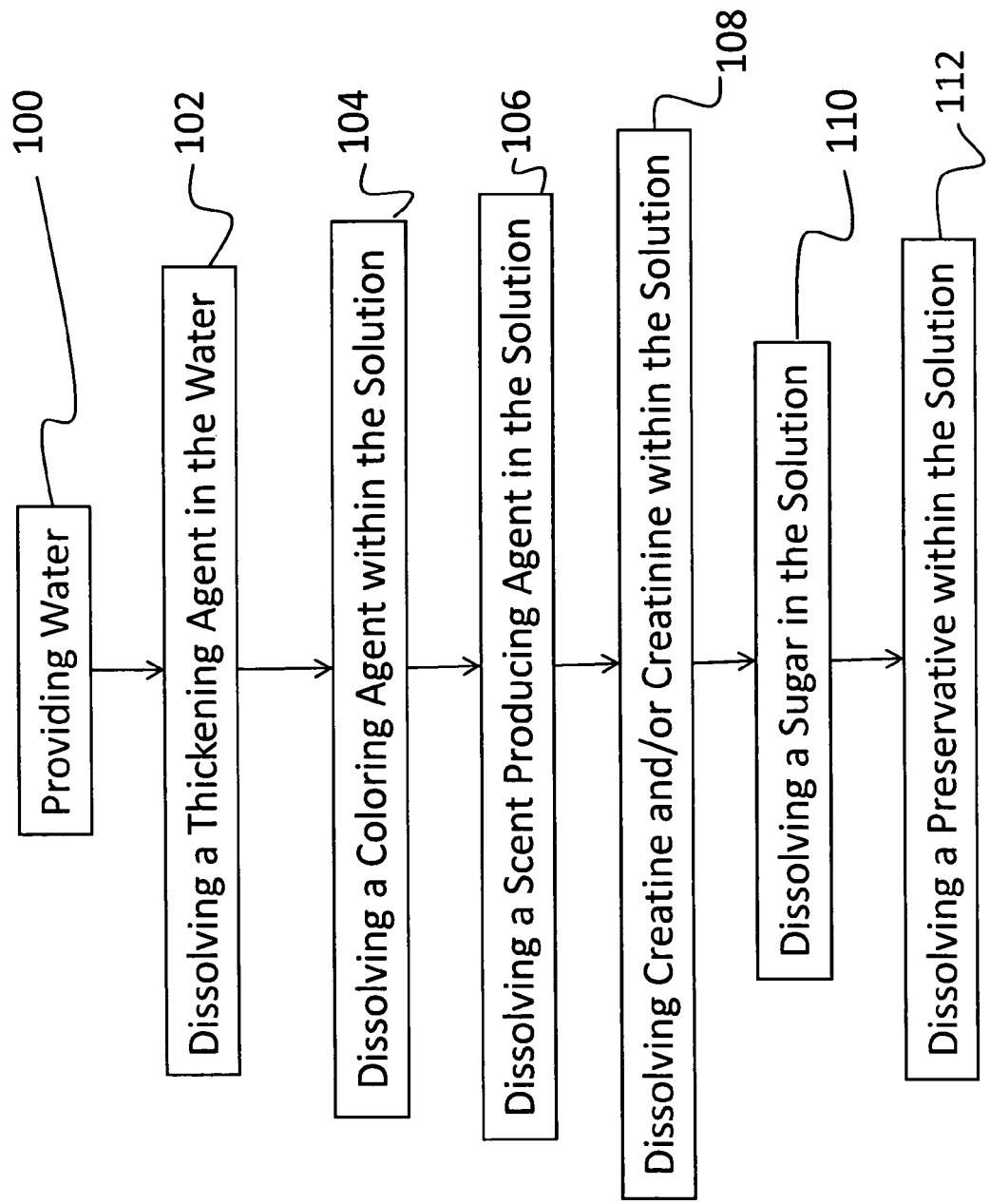

SYNTHETIC URINE AND METHOD FOR MANUFACTURING SYNTHETIC URINE

BACKGROUND OF THE INVENTION (1) Field of Invention

The present invention relates to a chemical composition and, more particularly, to a composition and method for manufacturing synthetic urine.

(2) Description of Related Art

Urinalysis is the analysis of urine to diagnose or detect a variety of medical conditions. Urinalysis is typically performed after the collection of a urine sample from an individual. A variety of tests can be performed on the urine sample to identify waste substances within the urine. Based on the waste substances, medical practitioners can often provide a medical diagnosis of the individual.

In some cases, drugs and other waste products are found in the urine samples. While such waste products can be useful in identifying which drugs are present in the individual, they can have an adverse impact on any medical diagnosis. Thus, it is useful to have a synthetic urine which is free of such waste products and which can provide a baseline for urinalysis.

While existing synthetic urine is useful for providing a baseline, it may not be consumer friendly. In other words, the synthetic urine may remain on a shelf for a period of time and, in some circumstances, may be inadvertently ingested by a consumer. Thus, to ensure marketplace safety, a need exists for a synthetic urine that is edible and shelf stable.

SUMMARY OF INVENTION

The present invention improves upon the prior art by providing a shelf stable, food grade synthetic urine solution. The synthetic urine solution includes water having a pH between 3 and 10. A thickening agent is dissolved within the water to form a solution having a specific gravity between $1.001$ $g/cm^3$ and $1.225$ $g/cm^3$. To provide aesthetic realism, a coloring agent (e.g., food coloring) is dissolved within the solution. Finally, to provide shelf stability, a preservative is dissolved within the solution.

In another aspect, the preservative includes acetic acid, calcium benzoate, calcium sorbate, carboxybenzene, citric acid, fumaric acid, lactic acid, methylparaben, natamycin, nisin, potassium acetate, potassium benzoate, propylparaben, sodium benzoate, sodium diacetate, sodium propionate, sodium sorbate, and sorbic acid, or any combination thereof in adequate amounts to render the solution shelf stable.

To operate as a baseline urine sample, creatine and/or creatinine is dissolved within the solution.

In yet another aspect, to provide olfactory realism, a scent producing agent (e.g., urea) is dissolved within the solution.

Thus, in one aspect, the synthetic urine solution is formed such that:
 a. the water is approximately 75 to 98 percent by volume of the solution;
 b. the thickening agent is approximately 0.1 to 2 percent by volume of the solution;
 c. the coloring agent is approximately 0.001 to 0.1 percent by volume of the solution;
 d. the urea is approximately 0.1 to 5 percent by volume of the solution;
 e. the creatinine is approximately 0.0 to 5 percent by volume of the solution;
 f. the creatine is approximately 0.0 to 5 percent by volume of the solution;
 g. a first preservative (e.g., lactic acid) is approximately 0.01 to 2 percent by volume of the solution;
 h. a second preservative (e.g., calcium sorbate) is approximately 0.001 to 2 percent by volume of the solution; and
 i. a third preservative (e.g., sodium diacetate) is approximately 0.01 to 2 percent by volume of the solution.

In yet another aspect, sugar dissolved within the solution.

Finally, as can be appreciated by one in the art, the present invention also comprises a method for forming and using the invention described herein.

BRIEF DESCRIPTION OF THE DRAWINGS

The objects, features and advantages of the present invention will be apparent from the following detailed descriptions of the various aspects of the invention in conjunction with reference to the following drawing, where:

FIG. 1 is a flow chart depicting a method for manufacturing a synthetic urine solution according to the present invention.

DETAILED DESCRIPTION

The present invention relates to a chemical composition and, more particularly, to a composition and method for manufacturing synthetic urine. The following description is presented to enable one of ordinary skill in the art to make and use the invention and to incorporate it in the context of particular applications. Various modifications, as well as a variety of uses in different applications will be readily apparent to those skilled in the art, and the general principles defined herein may be applied to a wide range of embodiments. Thus, the present invention is not intended to be limited to the embodiments presented, but is to be accorded the widest scope consistent with the principles and novel features disclosed herein.

In the following detailed description, numerous specific details are set forth in order to provide a more thorough understanding of the present invention. However, it will be apparent to one skilled in the art that the present invention may be practiced without necessarily being limited to these specific details. In other instances, well-known structures and devices are shown in block diagram form, rather than in detail, in order to avoid obscuring the present invention.

The reader's attention is directed to all papers and documents which are filed concurrently with this specification and which are open to public inspection with this specification, and the contents of all such papers and documents are incorporated herein by reference. All the features disclosed in this specification, (including any accompanying claims, abstract, and drawings) may be replaced by alternative features serving the same, equivalent or similar purpose, unless expressly stated otherwise. Thus, unless expressly stated otherwise, each feature disclosed is only one example of a generic series of equivalent or similar features.

Furthermore, any element in a claim that does not explicitly state "means for" performing a specified function, or "step for" performing a specific function, is not to be interpreted as a "means" or "step" clause as specified in 35 U.S.C. Section 112, Paragraph 6. In particular, the use of "step of" or "act of" in the claims herein is not intended to invoke the provisions of 35 U.S.C. 112, Paragraph 6.

(1) DESCRIPTION

The present invention relates to a synthetic urine solution and, as depicted in FIG. 1, a method for forming such a solution. The synthetic urine provides a baseline for testing and diagnosis that is useful to diagnosticians and consumers alike. Further, to enhance marketplace safety, the synthetic urine is formed of non-toxic substances to provide an edible, shelf stable product.

As noted by Wikipedia.org, a typical medical urinalysis usually includes (1) a pH reading, (2) a specific gravity reading, and (3) a description of color and appearance. See Urinalysis, wikipedia.org/w/index.php?title=Urinalysis&oldid=323832743 (last visited Nov. 9, 2009).

In its most basic form, the synthetic urine solution includes water having any suitable pH and at any suitable volume. The pH of urine is normally in the range of 4.8 to 7.5. However, various conditions can expand this range; thus, as a non-limiting example, the pH of the solution (and the provided water 100) is between 3.0 and 10.0 and the water is approximately 75 to 98 percent, by volume, of the total solution.

A thickening agent 102 is dissolved within the water to form a solution having a suitable specific gravity. The specific gravity of urine is normally 1.001 to 1.028. Specific gravity is an expression of the weight of a substance relative to the weight of an equal volume of water. For example, water has a specific gravity of one. Thus, to increase the specific gravity such that it more closely resembles the specific gravity of urine, a sufficient amount of thickening agent is dissolved within the water. For example, a sufficient amount of thickening agent is dissolved within the water such that the solution has a specific gravity between 1.001 $g/cm^3$ and 1.225 $g/cm^3$. The thickening agent is any item capable of thickening the solution to fall within the said ranges. As non-limiting examples, the thickening agent can be salt, sugar, fructose, guar gum powder, cornstarch, arrow root, and/or food grade gum. Further, the thickening agent is present in a suitable volume to generate a specific gravity within the desired ranges (i.e., between 1.001 $g/cm^3$ and 1.225 $g/cm^3$). As a non-limiting example, the thickening agent is approximately 0.1 to 2.0 percent, by volume, of the solution.

As noted above, urinalysis also provides a description of the color and appearance of the urine. To provide aesthetic realism, a coloring agent 104 is dissolved within the solution in a sufficient quantity to cause the solution to take on the color/appearance of real urine. As a non-limiting example, the coloring agent is approximately 0.001 to 0.1 percent, by volume, of the solution. The coloring agent is any suitable material that is non-toxic and capable of providing coloring to a solution, a non-limiting example of which includes common food coloring.

Additionally, to provide olfactory realism, a scent producing agent 106 is dissolved within the solution in a sufficient quantity to cause the solution to smell similar to real urine. As a non-limiting example, the scent producing agent is approximately 0.1 to 5.0 percent, by volume, of the solution. The scent producing agent is any suitable material that is capable of providing a urinary scent, a non-limiting example of which includes urea (as urea is a component of real urine that provides a distinct urinary scent).

To provide further realism and baseline components for testing purposes, the synthetic urine includes creatine and/or creatinine 108 dissolved within the solution. Creatinine is a break-down product of creatine in muscle, and is usually produced at a fairly constant rate by the body (depending on muscle mass). Creatinine levels in the urine may be used to calculate the creatinine clearance, which is a measure of renal function. In urinalysis or urine drug tests, creatinine concentration is often checked to insure that the sample is pure. For example, a high creatinine level indicates a pure test while low amounts of creatinine in the urine indicate a manipulated test, either through the addition of water in the sample or by drinking excessive amounts of water. See Creatinine, wikipedia.org/w/index.php?title=Creatinine&oldid=324278065 (last visited Nov. 9, 2009).

Thus, the creatine and/or creatinine are dissolved within the solution to serve as a baseline and simulate a pure urine sample. As a non-limiting example, creatinine may be dissolved within the solution such that it is approximately 0.1 to 5 percent by volume of the solution, while creatine may be dissolved within the solution such that it is approximately 0.1 to 5 percent by volume of the solution.

To further match urine character realism, a sugar can be added to match glucose levels found in real urine. Thus, sugar 110 is also dissolved within the solution to approximate glucose levels found in real urine. As a non-limiting example, 0.1-15.0 milligrams of sugar can be dissolved per deciliter of solution.

To improve the shelf stability of the product, a preservative 112 is dissolved within the solution. The preservative can be a single preservative or a combination of preservatives, non-limiting examples of which include acetic acid, calcium benzoate, calcium sorbate, carboxybenzene, citric acid, fumaric acid, lactic acid, methylparaben, natamycin, nisin, potassium acetate, potassium benzoate, propylparaben, sodium benzoate, sodium diacetate, sodium propionate, sodium sorbate, and sorbic acid, or any combination thereof in adequate amounts to render the solution shelf stable. As a non-limiting example, the solution includes a first preservative, a second preservative, and a third preservative, such as lactic acid, calcium sorbate, and sodium diacetate, respectively.

The combination of preservatives are added to the solution in any suitable volume to provide suitable shelf stability to the solution. As a non-limiting example, the first preservative is approximately 0.01 to 2 percent by volume of the solution, the second preservative is approximately 0.001 to 2 percent by volume of the solution, and the third preservative is approximately 0.01 to 2 percent by volume of the solution. It should be understood that any of the preservatives listed in the paragraph above can be substituted in as the first, second and third preservatives, and in any combination, or volume, thereof.

As noted above, FIG. 1 is a flowchart depicting a method for forming a synthetic urine solution. It should be understood that the flowchart is for illustrative purposes only as the present invention is not intended to be limited thereto. Further, although the flowchart depicts a process flow, the acts depicted in the flowchart are not necessarily sequential steps as each depicted item can be re-arranged (or omitted) in any suitable manner to arrive at the present invention. Thus, the flowchart depicts but one example of many processes in which the synthetic urine solution of the present invention can be formed.

What is claimed is:
1. A synthetic urine solution, comprising:
water having a pH between 3 and 10;
a thickening agent dissolved within the water to form a solution having a specific gravity between 1.001 $g/cm^3$ and 1.225 $g/cm^3$;
a coloring agent dissolved within the solution;
a preservative dissolved within the solution, wherein the preservative includes at least a first and second preservative selected from a group consisting of calcium benzoate, calcium sorbate, carboxybenzene, fumaric acid, lactic acid, natamycin, nisin, potassium acetate, potassium benzoate, propylparaben, sodium benzoate, sodium diacetate, and sodium sorbate and
wherein the solution as a whole is edible and shelf stable.

2. The synthetic urine solution as set forth in claim 1, further comprising at least one of creatinine and creatine dissolved within the solution.

3. The synthetic urine solution as set forth in claim 2, further comprising a scent producing agent dissolved within the solution.

4. The synthetic urine solution as set forth in claim 3, wherein the scent producing agent is urea.

5. The synthetic urine solution as set forth in claim 4, wherein:
the water is approximately 75 to 98 percent by volume of the solution;
the thickening agent is approximately 0.1 to 2 percent by volume of the solution;
the coloring agent is approximately 0.001 to 0.1 percent by volume of the solution;
the urea is approximately 0.1 to 5 percent by volume of the solution;
the creatinine is approximately 0.1 to 5 percent by volume of the solution;
the creatine is approximately 0.1 to 5 percent by volume of the solution;
a first preservative is approximately 0.01 to 2 percent by volume of the solution;
a second preservative is approximately 0.001 to 2 percent by volume of the solution; and
a third preservative is approximately 0.01 to 2 percent by volume of the solution.

6. The synthetic urine solution as set forth in claim 5, further comprising a sugar dissolved within the solution.

7. The synthetic urine solution as set forth in claim 4, wherein:
the water is approximately 75 to 98 percent by volume of the solution;
the thickening agent is approximately 0.1 to 2 percent by volume of the solution;
the coloring agent is approximately 0.001 to 0.1 percent by volume of the solution;
the urea is approximately 0.1 to 5 percent by volume of the solution;
a first preservative is approximately 0.01 to 2 percent by volume of the solution;
a second preservative is approximately 0.001 to 2 percent by volume of the solution; and
a third preservative is approximately 0.01 to 2 percent by volume of the solution.

8. The synthetic urine solution as set forth in claim 1, further comprising a scent producing agent dissolved within the solution, wherein the scent producing agent is urea.

9. The synthetic urine solution as set forth in claim 1, further comprising a sugar dissolved within the solution.

10. A synthetic urine solution, comprising:
water having a pH between 3 and 10;
a thickening agent dissolved within the water to form a solution having a specific gravity between 1.001 g/cm$^3$ and 1.225 g/cm$^3$;
urea dissolved within the solution;
a coloring agent dissolved within the solution; and
a preservative dissolved within the solution, wherein the preservative includes a first preservative, a second preservative, and a third preservative, wherein the first preservative, second preservative, and third preservative are selected from a group consisting of calcium benzoate, calcium sorbate, carboxybenzene, fumaric acid, lactic acid, natamycin, nisin, potassium acetate, potassium benzoate, propylparaben, sodium benzoate, sodium diacetate, and sodium sorbate; and
wherein the solution as a whole is edible and shelf stable.

11. A method for forming a synthetic urine solution, comprising acts of:
providing water;
dissolving a thickening agent within the water to form a solution having a specific gravity between 1.001 g/cm$^3$ and 1.225 g/cm$^3$;
dissolving a coloring agent within the solution; and
dissolving a preservative within the solution, wherein the preservative includes at least a first and second preservative selected from a group consisting of calcium benzoate, calcium sorbate, carboxybenzene, fumaric acid, lactic acid, natamycin, raisin, potassium acetate, potassium benzoate, propylparaben, sodium benzoate, sodium diacetate, and sodium sorbate; and
wherein the solution as a whole is edible and shelf stable.

12. The method as set forth in claim 11, further comprising an act of dissolving at least one of creatinine and creatine within the solution.

13. The method as set forth in claim 12, further comprising an act of dissolving a scent producing agent within the solution.

14. The method as set forth in claim 13, wherein in dissolving the scent producing agent, the scent producing agent is urea.

15. The method as set forth in claim 14, wherein in forming the solution:
the water is approximately 75 to 98 percent by volume of the solution;
the thickening agent is approximately 0.1 to 2 percent by volume of the solution;
the coloring agent is approximately 0.001 to 0.1 percent by volume of the solution;
the urea is approximately 0.1 to 5 percent by volume of the solution;
the creatinine is approximately 0.1 to 5 percent by volume of the solution;
the creatine is approximately 0.1 to 5 percent by volume of the solution;
a first preservative is approximately 0.01 to 2 percent by volume of the solution;
a second preservative is approximately 0.001 to 2 percent by volume of the solution; and
a third preservative is approximately 0.01 to 2 percent by volume of the solution.

16. The method as set forth in claim 14, wherein in forming the solution:
the water is approximately 75 to 98 percent by volume of the solution;
the thickening agent is approximately 0.1 to 2 percent by volume of the solution;
the coloring agent is approximately 0.001 to 0.1 percent by volume of the solution;
the urea is approximately 0.1 to 5 percent by volume of the solution;
a first preservative is approximately 0.01 to 2 percent by volume of the solution;
a second preservative is approximately 0.001 to 2 percent by volume of the solution; and
a third preservative is approximately 0.01 to 2 percent by volume of the solution.

* * * * *